United States Patent [19]

Unger et al.

[11] Patent Number: 4,990,132
[45] Date of Patent: Feb. 5, 1991

[54] METHOD AND APPARATUS FOR PLASMAPHERESIS

[75] Inventors: Peter Unger, Stockholm; Eric Westberg, Lidingö, both of Sweden

[73] Assignee: Omega Mediciteknik AB, Sweden

[21] Appl. No.: 275,056

[22] PCT Filed: May 13, 1987

[86] PCT No.: PCT/SE87/00240

§ 371 Date: Nov. 15, 1988

§ 102(e) Date: Nov. 15, 1988

[87] PCT Pub. No.: WO87/06844

PCT Pub. Date: Nov. 19, 1987

[30] Foreign Application Priority Data

May 16, 1986 [SE] Sweden .............................. 8602242-3
Dec. 18, 1986 [SE] Sweden .............................. 8605456-6

[51] Int. Cl.$^5$ .......................... A61M 37/00; B04B 5/00
[52] U.S. Cl. ............................................. 604/6; 494/17
[58] Field of Search ................. 604/6, 5; 494/17, 18, 494/35, 45

[56] References Cited

U.S. PATENT DOCUMENTS 4,268,393  5/1981  Persidsky ................................. 604/6
4,421,503 12/1983  Latham, Jr. et al. ................. 494/17
4,482,342 11/1984  Lueptow et al. ...................... 494/45

Primary Examiner—Stephen C. Pellegrino
Attorney, Agent, or Firm—Hill, Van Santen, Steadman & Simpson

[57] ABSTRACT

A method for plasmapheresis includes withdrawal of a quantity of blood from a blood donor to an annular primary container forming part of a closed flexible processing assembly positioned in a processing space provided in a centrifuge rotor and conformed to the processing assembly. During the withdrawal, the rotor is caused to perform an oscillating movement for agitating the blood whereupon the blood is centrifuged in the primary container to be separated into blood cells and plasma. While the centrifugation is going on, the primary container is compressed to expel the plasma fraction to a secondary container. Liquid diluent is then fed to the primary container to resuspend the blood cell fraction while agitation is again accomplished by oscillating the rotor, whereupon the blood cell fraction is returned to the blood donor. The apparatus is a closed flexible processing assembly for use in carrying out the method according to the invention and includes an annular primary container, a secondary container positioned in the central region of the annular primary container, a collapsible connecting duct connecting the portion of the primary container closest to the center of rotation with the secondary container, and a flexible tube connected to the primary container.

7 Claims, 2 Drawing Sheets

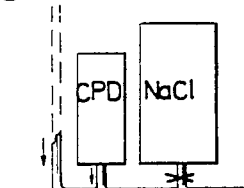
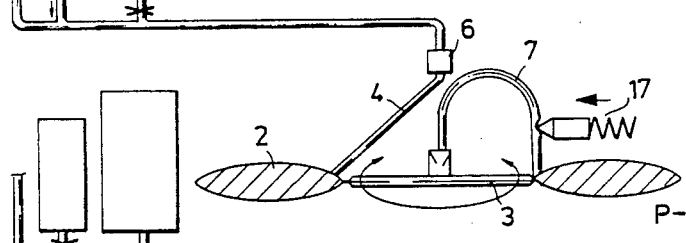
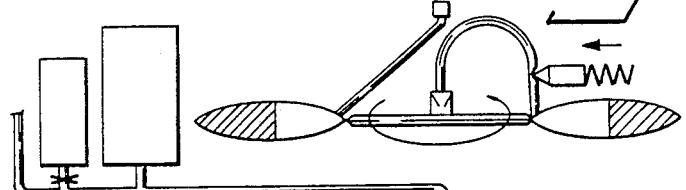
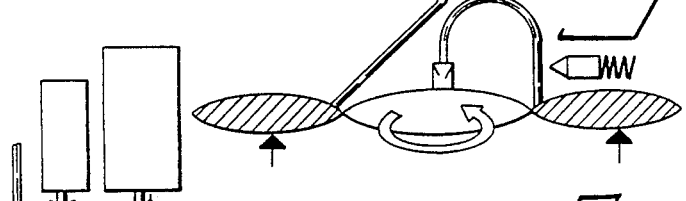
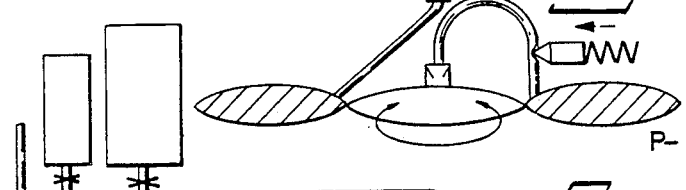
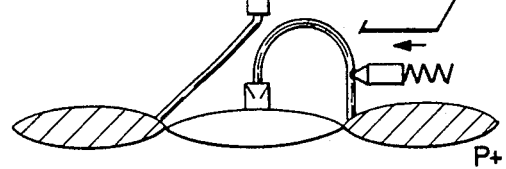

METHOD AND APPARATUS FOR PLASMAPHERESIS

METHOD AND APPARATUS FOR PLASMAPHERESIS

This invention relates to a method and an apparatus for carrying out plasmapheresis.

Half of the blood is so-called plasma, a yellowish liquid containing various proteins. The other half of the blood contains cellular material, such as red blood cells, white blood cells and platelets. Plasma is used in transfusions and as raw material for the pharmaceutical industry in connection with the production of pharmaceuticals, such as albumin, gamma globulin and Factor VIII (haemophilia medicament).

Plasma may be obtained in pure form by centrifugation, about 200 ml of red blood cells and about 250 ml of plasma being obtainable from a donated blood unit of about 500 ml, including anticoagulant. The plasma fraction can also be obtained by plasmapheresis, in which the blood of the blood donor is withdrawn and centrifuged whereupon the red blood cells are returned to the donor. Plasmapheresis is advantageous because it is a cheaper method of obtaining plasma in the case where red blood cells are not needed, because each withdrawal yields more plasma (in total 600 ml in the case of two-cycle plasmapheresis), and because plasmapheresis can be carried out more frequently than blood donation.

Relatively expensive automated equipment for plasmapheresis is known, such as the Haemonetic or Haemoscience machines which are made in the United States.

Apart from the high cost for the plasma production, these machines are only suitable for withdrawal in large blood banks, and for that reason plasmapheresis has to be carried out manually in most cases, especially when withdrawal is carried out in mobile units.

When plasmapheresis is carried out manually, blood is withdrawn from a blood donor (BG) and conveyed through a flexible tube to a bag positioned on a combined weighing scale and rocker. The scale discontinues the blood withdrawal and gives a warning when a sufficient amount of blood (about 450 ml) has been withdrawn, and the rocker mixes the blood with the anticoagulant. Thereupon the flexible tube is cut off under the action of heat so that the ends of the flexible tube are sealed, and the bag is carried to a centrifuge in which separation takes place. In the next step the bag is transferred to a squeezing device in which the plasma collected in the upper portion of the bag is expelled into a different bag. Saline is then added to the original bag containing the blood cells which are retransfused to the blood donor. Normally, this procedure is repeated with one and the same blood donor, that is, so-called two-cycle plasmapheresis is carried out, yielding 500–600 ml of plasma, including the originally added anticoagulant.

This system has many disadvantages:

Many manipulative steps including connections and disconnections of flexible tubes are required;

Separation of plasma from the centrifuged bag takes place manually and with the fractions held separated only under the action of the normal gravity, which means that high qualitY is not achieved, that is, that cellular material is left in the plasma. In order that high quality may be achieved, it is necessary to carry out repeated centrifugations and to transfer the plasma to a further secondary bag, which means added costs;

The method lends itself to confusion, because the bag is physically separated from the blood donor;

The method is time-consuming in that it takes about one hour. It is easy to recruit persons for donating blood, which takes about 15 minutes, but it is more difficult to find persons who can sacrifice one hour.

The object of the present invention is to provide a method and an apparatus permitting small-scale semiautomated utilization of plasmapheresis e.g. in mobile units, such as blood buses, and having the following advantages over manual plasmapheresis:

Increased speed;

Improved plasma quality (fewer cells left in the plasma);

Simplified procedure and reduced number of manipulative steps.

Increased safety because of reduced danger of confusion;

A large stationary centrifuge can be dispensed with.

This object is achieved by a method and an apparatus as defined in the claims.

When carrying out the method according to the invention, a centrifuge of the type described in Swedish patent application No. 8602242-3 may be used. This patent application discloses a centrifuge in which the processing space of the rotor includes an annular separation compartment and a central compartment. The volume of the separation compartment can be reduced during the centrifugation to displace a centrifugally separated component into the central compartment. An oscillating reciprocatary movement can be imparted to the rotor, and the processing space can be subjected to overpressure or vacuum.

When carrying out the method according to the present invention, blood is withdrawn from the blood donor direct into an annular primary container forming part of a closed flexible processing assembly which is positioned in the processing space of the centrifuge rotor. The centrifuge may be positioned immediately adjacent the blood donor coach. During the withdrawal the rotor is oscillated to mix the blood with anticoagulant with which the primary container has been primed beforehand or which is supplied at the same time as the blood. The next step consists in centrifugation of the blood in the primary container to separate blood cells and plasma. After a given centrifuging time, the plasma is expelled to a secondary container forming part of the processing assembly and disposed in the central region of the annular primary container. This transfer of the plasma may preferably be affected by increasing the rotational speed of the centrifuge so that a centrifugally operated valve opens a connecting duct between the primary container and the secondary container and at the same time subjecting the primary container to a squeezing pressure. Thereupon the centrifugation is discontinued, and liquid diluent (physiological saline) is fed to the primary container while agitation is again effected by oscillating the rotor, and the thus resuspended blood cell fraction is retransfused to the blood donor.

The invention also relates to a closed flexible processing assembly for use in carrying out the method. The processing assembly comprises an annular primary container, a secondary container positioned in the central region of the annulus, and a closable connecting duct between the portion of the primary container closest to the center of rotation and the secondary container, and a flexible tube connected to the primary container for supply of blood to the processing assembly and withdrawal of blood cell suspension from the processing assembly.

The invention will be described in greater detail hereinafter with reference to the accompanying drawings, in which:

FIGS. 4a–4e show the various steps of the method according to the invention.

Figure 1:
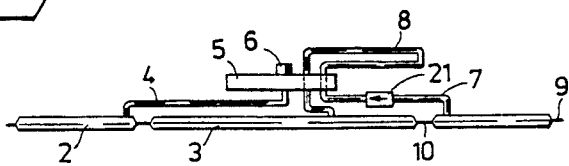
FIG. 1 is an elevational view of one embodiment of a processing assembly according to the invention.
Figure 2:
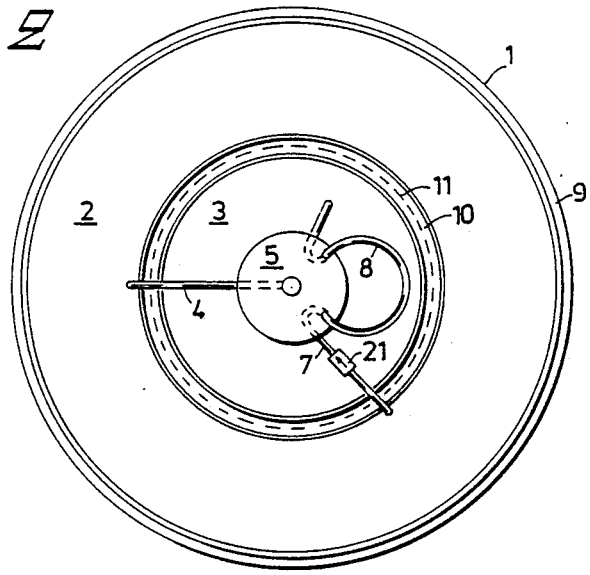
FIG. 2 is a plan view of the processing assembly.

FIGS. 1 and 2 show a processing assembly 1 comprising an annular primary container 2 and a secondary container 3 in the center of the annulus. A flexible tube 4 is connected to the primary container, passes through a sealing body 5 and ends in a sterile connector 6. A collapsible flexible tube 7 connects the portion of the primary container 2 closest to the center of rotation with the secondary container 3. The flexible tube 7 is provided with a check valve 21 which permits liquid flow from the primary container to the secondary container but closes to flow in the opposite direction. The flexible tube 7 is also passed through the sealing body 5 and forms a loop 8 on its outer side and then returns through the sealing body. The sealing body 5, which may consist of a rubber stopper, for example, serves to seal the separation space of the rotor from the surrounding atmosphere after the processing assembly has been brought in position in the separation space.

The processing assembly can be made from pieces of plastic foil which are interconnected by an outer annular joint 9 and an inner annular joint 10. In this way, an annular primary container 2 and a disc-like secondary container 3 in the central region of the annulus are formed. Suitably, the inner joint is provided with a perforation 11 in the middle so that the containers can be disconnected from one another. The plastic foil preferably is made of PVC or polyethylene, and the joining can be effected by heat sealing in well-known manner. The flexible tubes 4 and 7 are welded in similar manner to the plastic sheet, if desired with a reinforcing neck at the point of attachment.

Figure 3:
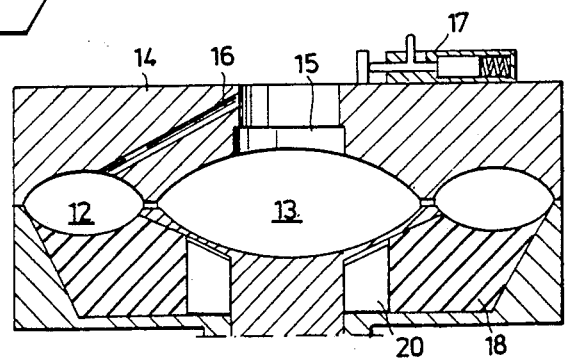
FIG. 3 is a diagrammatical cross-sectional view of the centrifuge rotor according to SE 8602242-3.

FIG. 3 is a diagrammatic cross-section of a rotor which is suitable for use in carrying out the present invention. A centrifuge rotor of the illustrated design is described in greater detail in Swedish patent application No. 8602242-3. The processing assembly 1 is positioned in the processing space 12, 13 of the rotor. Numeral 12 designates an annular separation compartment and numeral 13 designates a central compartment communicating with the separation compartment. In the cover 14 of the rotor there is an opening 15 above the central compartment. When the processing assembly has been brought in position in the rotor, this opening is sealed by pulling the sealing body 5 upwardly into the opening 15 whereupon the processing space of the rotor may be subjected to overpressure or vacuum by way of a connection 16. When this is done, the valved connector 6 of the flexible tube 4 and the tube loop 8, which is inserted in a centrifugally operated pinch valve 17, are positioned outside the sealed separation space. A pressure medium 18, e.g. a rubber body, is deformed as a result of the centrifugation and exerts a pressure on the primary container 2 positioned in the separation compartment 12. The rotor is driven by a programme-controlled motor (not shown).

In use of the apparatus of FIGS. 1 and 2, a processing assembly is positioned in the rotor, and the processing space of the rotor is sealed by means of the sealing body 5. The tube loop 8 is inserted in the pinch valve 17. FIGS. 4a–4e show the various steps of the procedure which is then carried out.

FIG. 4a shows withdrawal of blood during agitation. The connector 6 is attached to a standard withdrawal kit which is also linked to a blood donor (BG). Blood is withdrawn from the blood donor and at the same time anticoagulant (CPD) is added. Alternatively, if only single-cycle plasmapheresis is to be carried out, the primary container may be primed with anticoagulant beforehand. When two-cycle plasmapheresis is carried out, anticoagulant is continuously supplied through the blood withdrawal kit as shown in FIG. 4 or by priming the primary container with one unit of anticoagulant. If the negative hydrostatic pressure from the blood donor to the primary container is insufficient for normal withdrawal of blood, the processing space of the centrifuge may be subjected to vacuum. In the centrifuge according to SE 8602246-3 a vacuum pump is connected to the passage 16 (FIG. 3) to provide the desired increased vacuum. The blood of the donor now flows into the primary container 2. To ensure that the anticoagulant is thoroughly mixed with the blood, the centrifuge is programmed during this phase to oscillate the rotor at a predetermined amplitude and a predetermined frequency.

The primary container suitably is designed to accommodate a blood donation (usually 500 ml) so that the withdrawal of the blood is discontinued automatically when this quantity has been withdrawn. The centrifuge may be equipped with an alarm device which is activated when the primary container has been filled. Attention is thereby called to an attendant who disconnects the blood withdrawal kit from the connector 6, and in the customary manner saline is fed to the blood donor to replace a portion of the withdrawn blood and to keep the blood withdrawal tubes clean. At the same time, the centrifuging step I (FIG. 4b) is initiated by switching the centrifuge from oscillation to rotation, and the rotor is accelerated to a selected separation speed. In centrifuging step I the blood cells settle in the peripheral part of the primary container while the plasma is collected in the portion of the annulus 2 closest to the center. In this step the connecting tube 7 is kept closed by the centrifugal valve 17, for example.

After a calculated time has elapsed, centrifuging step II (FIG. 4c) is initiated. In this step the separated plasma is caused to flow to the secondary container 3 by way of the check valve 21. This is accomplished by reducing the volume of the separation compartment while the centrifugation is going on so that the primary container 2 is compressed and the plasma fraction is displaced to the secondary container 3. In one embodiment of the centrifuge described in SE 8602242-3, this is done with the aid of a rubber body 18 (FIG. 3) positioned in the rotor, which rubber body has greater density than the blood and/or is acted on by radially displaceable weight segments. During the centrifugation the rubber body exerts a pressure on the primary container in the separation compartment. However, the centrifuged blood volume cannot move, because the valve 17 is closed. While centrifuging step II is carried out, the valve 17 is opened and the rubber body 18 is deformed into the separation compartment and expels a corresponding volume of plasma into the secondary container. In accordance with a preferred embodiment, centrifuging step II is carried out at a higher centrifuge speed than centrifuging step I. The transfer of the plasma then takes place while the separated phases are subjected to the action of a centrifugal field which is even stronger than that existing during the settling phase (centrifuging step I). The danger of resuspending blood cells in the plasma fraction during the transfer therefore is very small. When two centrifuge speeds are used, the valve 17 may be a centrifugal valve set to be closed at the lower speed and to open at the higher speed. The rubber body 18 and the weight segments or corresponding means may also be adapted to provide the required transfer pressure only when the higher speed has been reached.

The transfer may also by monitored by photocells, e.g. at the tube loop 8, which then has to be transparent. If cells reach the light path of the photocell, the transfer is discontinued, e.g. by reducing the centrifuge speed so that the centrifugal valve 17 closes and/or the pressure action of the rubber body ceases.

After a predetermined time has elapsed, the centrifuge is stopped and the resuspension step is initiated (FIG. 4d). Liquid diluent (physiological saline) is now fed to the primary container by way of the connector 6 while the rotor is again oscillated. The processing space of the centrifuge may then be subjected to vacuum in the same way as during the withdrawal of blood so that the introduction of the saline into the primary container is facilitated. When the cell concentrate remaining in the primary container has been diluted to the desired concentration, the retransfusion step (FIG. 4e) is commenced. A new flexible tube is attached to the connector 6, and the processing space on the rotor is subjected to a predetermined overpressure, e.g. by pumping air into it by way of the passage 16. The contents of the primary container then flow through the attached flexible tube by way of an air trap and a connected transfusion kit with a filter and back to the blood donor. When the primary container 2 is empty, a single-cycle plasmapheresis is completed. When two-cycle plasmapheresis is carried out, the secondary container 3 is made large enough to accommodate two batches of plasma, and the procedure is repeated with the same processing assembly. The cover 14 is then removed, and the flexible tube 7 is sealed and cut. e.g. by means of a pair of heat-sealing jaws. The secondary container with the recovered plasma is torn away from the primary container along the perforation 11 of the joint 10. Then the secondary container can immediately be frozen to save the quality of the plasma.

We claim:

1. A method for carrying out plasmapheresis comprising the steps of:
    withdrawing a quantity of blood from a blood donor to an annular primary container forming part of a closed flexible processing assembly positioned in a processing space in the rotor of a centrifuge, said processing space being conformed to the processing assembly;
    agitating the motor during withdrawal of the blood and thereby also agitating the blood;
    centrifuging the blood in the primary container and thereby separating the blood into blood cells and plasma;
    compressing the primary container during centrifuging and thereby expelling the plasma to a secondary container disposed in a central region of the annular primary container;
    simultaneously feeding liquid diluent to the primary container and agitating said primary container with the rotor and thereby resuspending said blood cells, and
    returning the suspended blood cells to the blood donor.

2. A method according to claim 1, wherein the step of centrifuging the blood is further defined by centrifuging the blood at a first speed with a collapsible connecting duct between the primary container and the secondary container being closed and increasing the rotational speed of the rotor to a second rotational speed at which the connecting duct is open.

3. A method according to claim 1, comprising the additional step of subjecting the processing space of the rotor to a vacuum during the withdrawal of blood to the primary container.

4. A method according to claim 1, comprising the additional step of pressurizing the processing space of the rotor during the returning of the blood cells to the blood donor.

5. In a closed flexible processing assembly for use in carrying out plasmapheresis by withdrawing a quantity of blood from a blood donor into a primary container, centrifugally separating the blood in the primary container into a plasma fraction and a blood cell fraction, transferring the plasma fraction from the primary container into a secondary container, and returning the blood cell fraction from the primary container to the donor, the improvement of said processing assembly being adapted to be received in a processing space in a centrifuge rotor and comprising the following:
    an annular primary container;
    a secondary container surrounded by the primary container;
    a tubular connecting duct providing communication of the radially inner portion of the primary container with the secondary container; and
    a flexible tube connected to the primary container for conveying blood into the primary container;
    wherein said primary and secondary containers comprise pieces of plastic foil joined together by an outer annular joint and an inner annular joint.

6. A processing assembly according to claim 5, wherein said tubular connecting duct includes a check valve permitting liquid flow from the primary container to the secondary container.

7. A processing assembly according to claim 5, wherein said inner annular joint is perforated whereby said containers can readily by disconnected from one another.

* * * * *